United States Patent [19]

Jolesz et al.

[11] Patent Number: 5,131,392

[45] Date of Patent: Jul. 21, 1992

[54] USE OF MAGNETIC FIELD OF MAGNETIC RESONANCE IMAGING DEVICES AS THE SOURCE OF THE MAGNETIC FIELD OF ELECTROMAGNETIC TRANSDUCERS

[75] Inventors: Ferenc A. Jolesz, Chestnut Hill; Peter D. Jakab, Sharon, both of Mass.

[73] Assignee: Brigham & Women's Hospital, Boston, Mass.

[21] Appl. No.: 479,415

[22] Filed: Feb. 13, 1990

[51] Int. Cl.⁵ ............................................. A61B 5/055
[52] U.S. Cl. ............................... 128/653.2; 128/653.5; 128/24 EL; 606/128; 324/309
[58] Field of Search ........ 128/660.03, 24 EL, 24 AA, 128/653 A, 653 SC; 324/309, 300; 606/127, 128

[56] References Cited

U.S. PATENT DOCUMENTS

| | | |
|---|---|---|
| 4,262,632 | 4/1981 | Hanton et al. |
| 4,413,233 | 11/1983 | Fossel et al. |
| 4,436,684 | 3/1984 | White |
| 4,543,959 | 10/1985 | Sepponer ................ 128/653 A |
| 4,576,777 | 3/1986 | Weber |
| 4,651,099 | 3/1987 | Vinegar et al. ............ 128/653 SC |
| 4,672,972 | 6/1987 | Berke |
| 4,691,163 | 10/1987 | Blass et al. |
| 4,712,057 | 12/1987 | Pau |
| 4,718,431 | 1/1988 | Hartl et al. |
| 4,723,536 | 2/1988 | Rauscher et al. |
| 4,777,464 | 10/1988 | Takabashita et al. ........... 324/318 |
| 4,805,626 | 2/1989 | Di Massimo et al. ......... 127/653 SC |
| 4,816,766 | 3/1989 | Zabel ........................ 128/653 SC |

OTHER PUBLICATIONS

Reichenberger et al., in their *Siemano Research and Development Report*, titled "Electromagnetic Acoustic Source for the Extracorporeal Generation of Shock Waves in Lithotripsy" (1986, vol. 15, 187-194).

Pemberton, *Extracorporeal Shockwave Lithotripsy*, Postgraduate Medical Journal (vol. 63, 1025-1031) (1987).

Schad et al., *Correction of Spatial Distortion in MR Imaging: A Prerequisite for Accurate Stereotaxy*, Journal of Computer assisted Tomography (vol. 11, 499-505) (1987).

Fuchs et al., *Extracorporeal Shockwave Lithotripsy-An Update*, Endourology (vol. 2, 1-8) (1987).

*Primary Examiner*—Ruth S. Smith
*Attorney, Agent, or Firm*—Sterne, Kessler, Goldstein & Fox

[57] ABSTRACT

A magnetic resonance imaging device is used to provide the static magnetic field for transducers. The static magnetic field in combination with electric current pulses energize phased arrayed transducers to generate acoustic waves or motion. The transducers can be arranged in the magnetic resonance imaging device static magnetic field to focus acoustic shock waves for the disintegration of target calculi in extracorporeal shock wave lithotripsy. The magnetic resonance imaging device is also used for target localization and monitoring of the mechanical energy effects of the transducers. In further embodiments, the transducers include coils that are implantable within a subject body and can be moved in the magnetic resonance imaging device's static magnetic field.

16 Claims, 4 Drawing Sheets

USE OF MAGNETIC FIELD OF MAGNETIC RESONANCE IMAGING DEVICES AS THE SOURCE OF THE MAGNETIC FIELD OF ELECTROMAGNETIC TRANSDUCERS

BACKGROUND OF THE INVENTION

A. Field of the invention

This invention constitutes a bridging of two commercially important fields in modern medical technology, namely magnetic resonance imaging (MRI), and extracorporeal shock wave lithotripsy (ESWL) to open up a new domain of nonsurgical treatments. The invention is the use of the static magnetic field of an MRI device for purposes other than imaging, specifically as a component of electromagnetic transducers and the use of the MRI device for automated control of procedures. The transducers may be used for the generation of shock waves for extracorporeal lithotripsy or for other applications of shock wave therapy or, in general for producing motion which may be useful in medical applications.

Related Art

Destroying various targets inside a human body with shock waves requires a specially designed instrument which is able to:

a) locate the target inside the human body;
b) generate a special acoustic pressure wave;
c) focus the acoustic pressure wave onto the target.

In the field of Extracorporeal Shock Wave Lithotripsy (ESWL) the usual targets are renal or gall-stones. These targets first must be located and positioned in the focal area of the shock wave generator. Then, by applying a set of powerful acoustic shock waves through the surface of the human body in such a way that the pressure increases at the target, the stones can be fragmented. Weak acoustic waves travel through the soft tissues without any damage as long as the pressure remains below a certain level. Focusing acoustic waves produces pressure above a given threshold to destroy targets.

Current commercial lithotripsy systems use X-ray or acoustic imaging techniques (ultrasound) to locate the target. X-ray imaging exposes the patient to ionizing radiation, and non-calcified stones which are most effectively treated with ESWL are not seen. Ultrasound is limited by poor image quality, including artifacts produced when imaging stones and stone fragments.

There are three common methods currently employed for shock wave generation: the spark generator, the piezo-electric array, and the electromagnetic acoustic generator.

Spark generators are used to create powerful electric sparks to generate shock waves. The poor focusing ability of the spark generator results in soft tissue damage around the stone. Another drawback of this technique stems from the rapid burn out rate of the electrodes of the spark generator, requiring replacement after each procedure. Piezo-electric generators build up shock waves by the displacement of a mosaic array of piezo-electric crystals. Even with large array size and good focusing, the shock waves achieve only a moderate pressure at the focal point, and therefore, are unable to break up larger calculi within a reasonable time.

Electromagnetic acoustic shock wave generators have been developed for implementation in this field. The early stage of this development is disclosed by Reichenberger et al. in their *Siemens Research and Development Report*, titled "Electromagnetic Acoustic Source for the Extracorporeal Generation of Shock Waves in Lithotripsy." (1986, vol. 15, 187-194). The electromagnetic acoustic source lithotripter includes a discharge capacitor as a power supply. An enameled copper wire slab coil is suspended by a ceramic support. The coil is separated from a metallic membrane by a thin insulating film. The coil and the conductive membrane act as the primary and secondary windings of a transformer. Upon application of a current to the coil via the discharge power supply, eddy currents are induced in the membrane which result in a repulsive force between the coil and the membrane. The membrane is thus caused to emit an acoustic pulse which is then focused on the target by an acoustic lens.

SUMMARY OF THE INVENTION

This invention adapts the MRI device to function with a lithotripter. The invention provides a novel solution for target localization and for acoustical pressure wave generation. The invention uses computer-aided real-time feedback from an image of the target to furnish positioning and focusing information to facilitate target destruction.

The magnetic and radio frequency fields of the MRI device are utilized to determine position or potential motion of a target (stones, tumors or other destructible objects) by using existing MRI imaging techniques. This provides excellent contrast of the target. Unlike known MRI devices, the present invention includes a transducer which converts electrical energy to mechanical energy in a form of motion or acoustical pressure involving the static magnetic field of the MRI device. Shock waves, special acoustical pressure waves, are generated when a charged capacitor, or equivalent energy supply, is connected to a conductive plate located within the MR imager's high static magnetic field. The discharge of the capacitor starts a current flow, which interacts with the static magnetic field and results in a force to act on the current carrier. The current carrier is attached to an acoustically transparent material which transmits the pressure wave, generated by the force, toward the target located in the human body, for example. The conductive plate may be shaped for only geometrical focusing, or alternatively, a set of plates may be arranged to make a phased-array. In a preferred embodiment, a combination of both methods can be used to generate a strong, well-focused acoustic pressure wave aimed at the target.

Information available from the images is used for the control of the procedure. Besides the localization of the target, damage to the surrounding tissues and the mechanical effect of the acoustic pressure wave at and around the focal point can be obtained from the images. Variables such as repetition rate, peak pressure amplitude, size of the focal area, the position of the focus point, and the position of the target itself can be changed to optimize the procedure. All these control functions can be performed by a human operator; however, the preferred embodiment utilizes a real-time computer-controlled system.

The adaptation of an MRI device to function as a lithotripter has a number of advantages. First, the fields of the MR imager are non-ionizing. Second, the transducer in the MRI device can furnish large amounts of energy in the form of acoustic pressure waves for breaking up hard targets such as renal and gall stones or for decimation of large sized tumors and other soft tissue targets. Other advantages of the MRI acoustic pressure generator include the large area available within the MRI for placement of transducers and the high magnetic field strength, thus enabling higher energy per pulse to be generated. Better accuracy of focusing with phased arrays under continuous computer control, and the potential to match the size of the target with the beam area are also achieved. The tumor decimation effect, causing cell death through cavitation, is important because it allows the present invention to be applied to the non-surgical treatment of tumors or other abnormal soft tissues. It may be possible to adapt this technique to the destruction of non-tumor cells, for example nerve cells or endocrine glands.

The use of the MRI device's static magnetic field as an alternative source of the magnetic component of the electromagnetic transducers has other practical applications as well. Transducers can function in a variety of ways. For example, implanted transducers can run pumps, electric motors or vibrators which can be housed in the human body or within catheters.

BRIEF DESCRIPTION OF THE DRAWINGS

The invention is best understood by reading the following detailed description in conjunction with the following drawings, in which.

DETAILED DESCRIPTION

Figure 1:
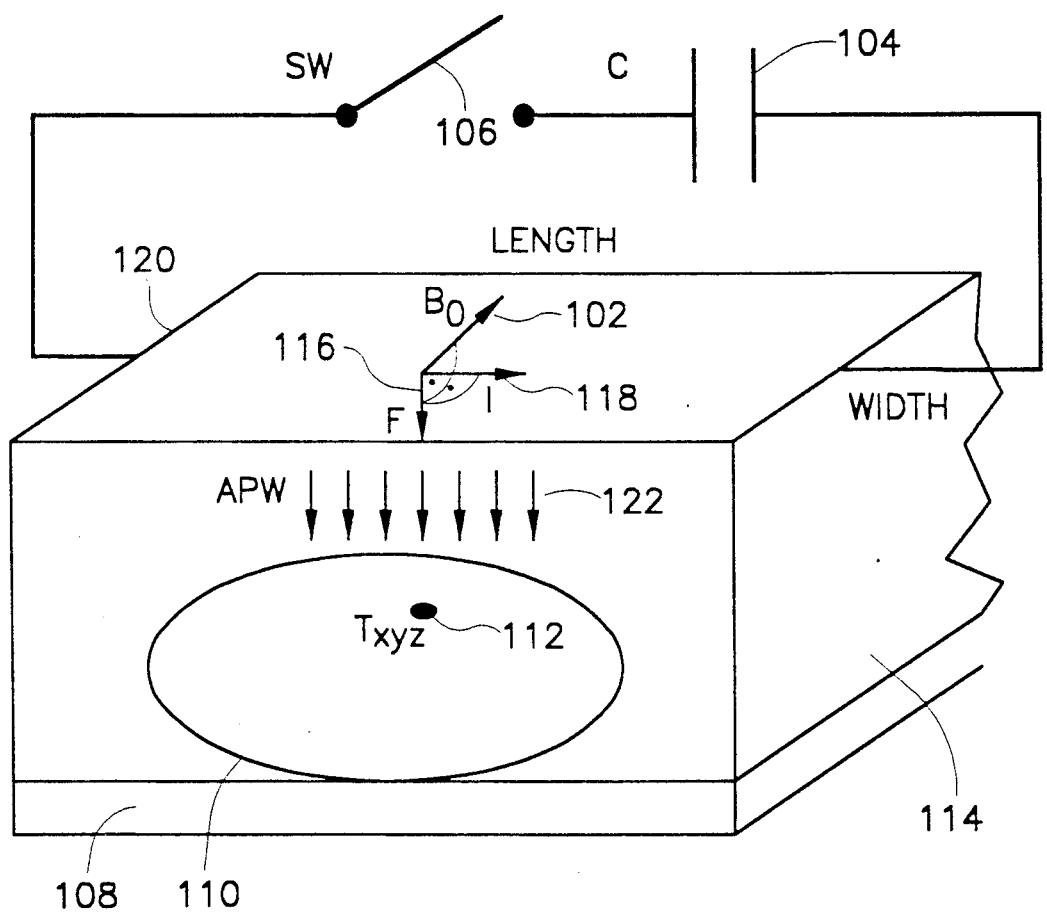
FIG. 1 is a schematic diagram of the way an MRI device's magnet produces acoustic pressure waves or motion according to the present invention.

In a preferred embodiment, the MRI device is modified for extracorporeal lithotripsy. Referring to FIG. 1, a static magnetic field $B_O$ of a magnetic resonance imaging device is represented by an arrow 102. A transducer plate 120 is electrically connected to a local energy storage device (a capacitor 104, for example) via a control device 106 (a controlled switch). The patient cradle 108 is movable through all three coordinate directions (x, y and z) and carries the patient 110 with hardened accumulation targets 112. An acoustically transparent medium 114 acoustically connects the surface of the human body to the transducer plate 120. The force F (116) acting on a conductor 120 of length l carrying current I (118) in a magnetic field of flux density B will be:

$$F = \int_0^1 I(dl \times B)$$

In a homogenous static magnetic field, when the magnetic flux density is $B_O$ (102) and the angle between the direction of $B_O$ and the direction of the current I (118) is $\phi$, the force which creates the acoustic pressure wave APW 122 will be:

$$F = B_O I l \sin\phi$$

In the case of an incompressible fluid (e.g., water) as the acoustically transparent medium 114, the acoustic pressure wave APW's amplitude P produced by the plate 120 (of width w) carrying current perpendicular to the direction of the magnetic field ($\phi = \pi/2$) is:

$$P = B_O I / w$$

Figure 2:
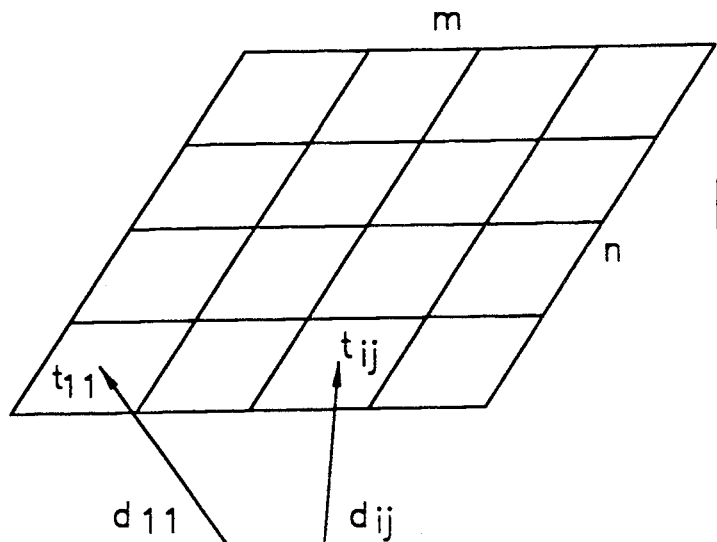
FIG. 2 shows a transducer comprised of a plurality of plates covering a flat surface according to the present invention.
Figure 3:
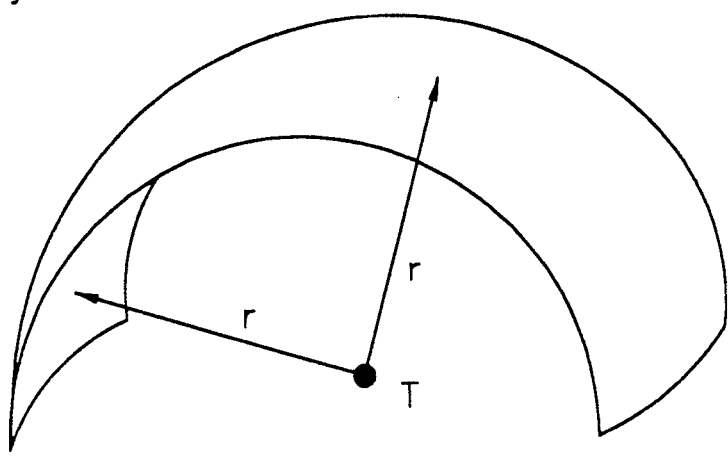
FIG. 3 shows a transducer comprised of one spherically shaped plate according to the present invention.

Focusing this acoustic pressure wave may be done by forming the transducer plate into a section of a sphere as shown in FIG. 3. Alternatively, focusing may be achieved by cutting the plate into small pieces, driving them with a different time-delayed current and placing them on a flat surface (see FIG. 2 for example) or any angled surface (see FIG. 4). These later examples are considered phased-arrays.

Suppose that in each case the total surface area covered by the source plates is the same ($A_s$) and the acoustic pressure wave arrives at the target surface (of area $A_t$) in phase. The pressure $P_t$ will be the sum of pressures from the source plates:

$$P_t = A_s/A_t \sum_{i=1}^{n} \sum_{j=1}^{m} c_{ij} P_{ij}$$

where $P_{ij}$ represents the pressure generated by the force acting on the plate $t_{ij}$, n is the number of rows and m is the number of columns. When the number of plates $N = nm$, the total source surface area is: $A_s = Na$ (if a is the unit surface area). The representation of the loss from the source to the target $c_{ij}$ depends upon the distance between the surface of the plate $t_{ij}$ and the target; the composition of the medium through which the pressure waves are transmitted (i.e., water and tissue); and the angle between the tangent of the surface and the direction from the source to the target. To achieve summing of the acoustic pressure wave at the target, the phase of the arriving waves must be the same.

In FIG. 3, only one spherically shaped plate generates the pressure waves. The focusing is purely geometrical. The surface is perpendicular at any point to the center of the sphere which becomes the focal point. The pressure amplitude loss, due to angular displacement if the tangent of the source plate is not perpendicular to the direction toward the target, is zero when the target is positioned precisely at the center. The distance between the source and the target is equal to the radius of the sphere. Therefore, there is no need for time-delayed firing of multiple plates.

Another embodiment is presented in FIG. 2, where the plates are arranged to create a flat surface. The focusing is based exclusively upon the phased-array method. The focal point is determined by the phase of the arriving waves, e.g., the firing sequence of the plates. The focal point can be calculated and partially moved, but in the case of most of the periphery plates of the array, there will be a loss due to the non-perpendicular direction of the plates' tangent. A time delay may be added to the firing time of plate A as compared to the firing time of the farthest plate B. This additional time delay can be calculated from the time necessary for the pressure wave to travel from the farthest plate B to the target. If the wave travels everywhere with the same speed, the time delay will only depend on the difference of distances from the i-th plate to the target and from the farthest plate to the target. Hence, because of the losses, the area where the focal point can be moved is limited. The angular loss is equal to the sine of the angle between the tangent of the plate and the direction of wave from the plate to the target. Hence, placing the plates in a tilted position can improve performance.

Figure 4:
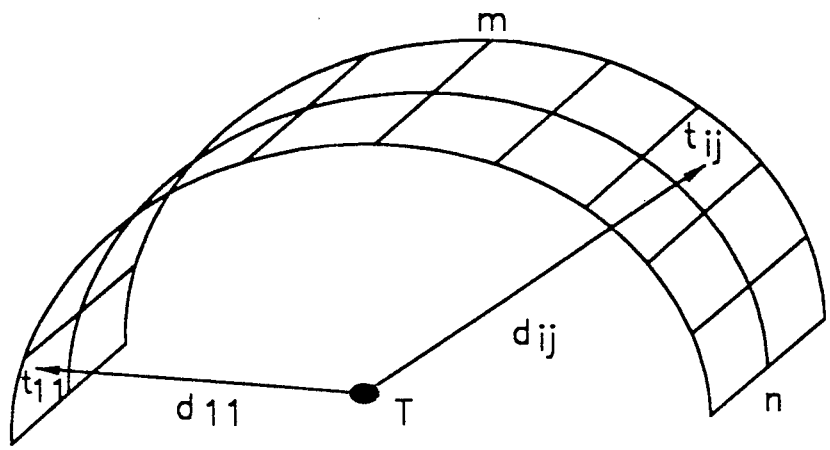
FIG. 4 shows a transducer comprised of a plurality of angled plates according to the present invention.

The combination of the previous methods is shown in FIG. 4. This embodiment enjoys higher efficiency and flexibility. The plates are arranged to be on or close to a surface of a sphere. Therefore, there is no significant loss of power due to the inappropriate angulation of the plates. The distance between individual surface points and the target may vary. In this case, independent firing of the plates may be necessary to achieve a phased-array. This enables spatial movement of the focal point and permits the focal point to remain on the target throughout the procedure.

Figure 5:
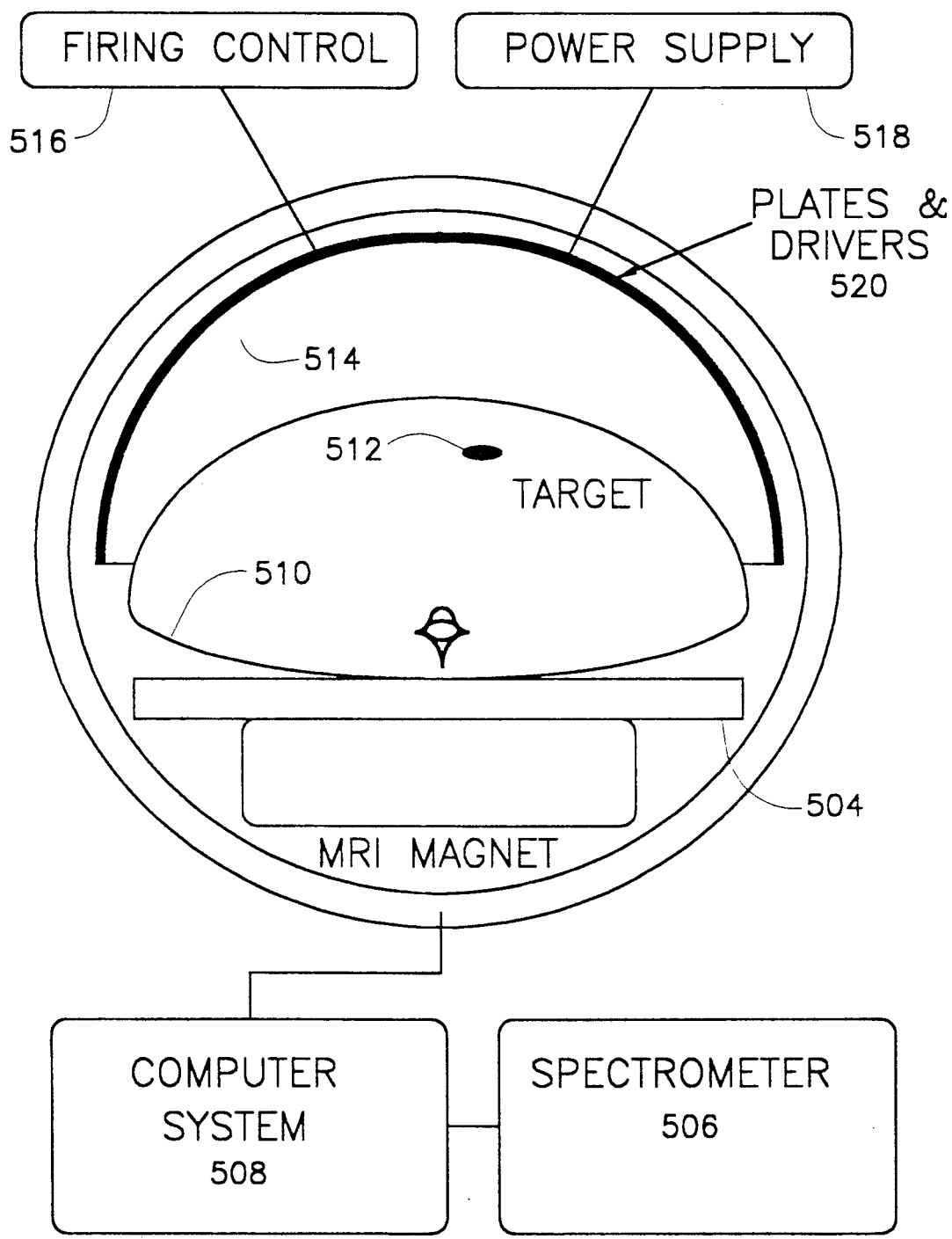
FIG. 5 is a diagrammatic representation of a lithotripsy system according to the present invention.

FIG. 5 depicts an MRI system adapted with the necessary tools for production and control of shock waves on a target in a human patient. The MRI system comprises a magnet 502 with gradient and RF coils, a patient cradle 504 on which the patient is positioned, a spectrometer 506 executes the MRI procedure, and computer system 508 for the control of the procedure, image reconstruction and display. The components of the system necessary for shock wave generation and targeting comprise plates 520 each with its driver(s), firing control unit 516, with a power supply 518 and a coupling balloon 514.

Figure 6:
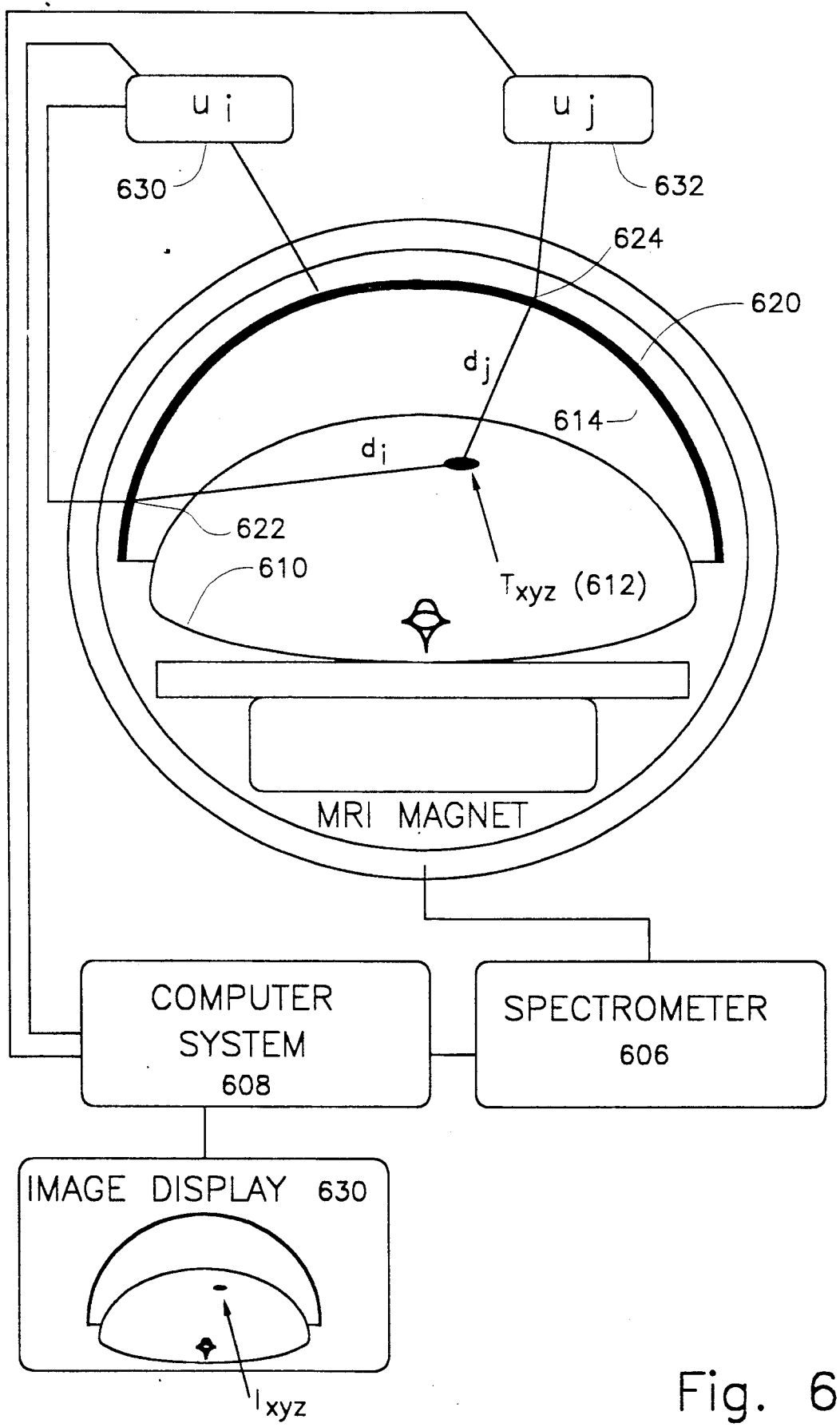
FIG. 6 is a diagrammatic illustration of a preferred embodiment of the present invention depicting the phased array method and a real-time computer control system therefor.

The treatment procedure may be better understood with reference to FIG. 6. In FIG. 6 reference numerals 606, 608, 610, 612, 614 and 620 correspond to reference numerals 506, 508, 510, 512, 514 and 520 in FIG. 5, respectively. Two driver control units $U_i$ and $U_j$ (630 and 632, respectively) are also shown in FIG. 6. Driver control units 630 and 632 represent sections of the firing control unit 516 of FIG. 5, which, in one embodiment, are used to drive individual plates 620. The computer system 608 invokes an MRI procedure with the spectrometer 606 under control of an operator. The basis of the procedure is the following: all MRI systems apply the same principles (reference General Electric Medical Systems Signa System operator manual OMS2 Rev. 12); MRI systems employ magnetic field gradients along all three orthogonal axes (x, y, z) in a sequence. The magnetic field gradient slightly alters the strength of the main magnetic field. Each type of nucleus has a unique gyromagnetic ratio ($\gamma$). This ratio, times the flux density of the magnetic field (B), determines the nucleus precessional frequency (f). The main magnetic field is altered by the field of the gradients, as the precession frequency is altered. Thus spatial location of a nucleus can be determined from the response to the radio frequency excitement, under a sequence of gradients. The coordinates of the target T(x,y,z) 612, available from the image display 630, directly correspond to the real spatial coordinates of target T(xyz) 612. The position of the transducer plates (with the driver circuits) 620, is also known by the computer system. The position of the transducer plates is either measured previously or determined from images, as would become apparent to those working in the art.

Due to the inhomogeneities of the main magnetic field and/or nonlinearity of the gradients, some correction is necessary when calculating the image coordinates to correspond to the spatial coordinates. This correction is either provided by the manufacturer of the magnet or can be determined by measurements. An article titled "Correction of Spatial Distortion in MR Imaging: A Prerequisite for Accurate Stereotaxy" authored by Schad, Lott, Schmitt, Sturm and Lorentz, in the May/Jun. 1987 *Journal of Computer Assisted Tomography*, 11(3):499-505 discusses the correction commonly used in the MRI-guided stereotactic surgery. Its disclosure is incorporated herein by reference as if reproduced in full below.

Once the target is identified with an electronic pointer on the image display, the spatial coordinates of the target will be available after computer-aided calculations. Repeated measurements can reveal the motion of the target, and the different travel path of the acoustic pressure wave from each of the elements of the transducer can be compensated in the firing sequence. A plate $p_i$ 622, for example, is a distance $d_i$ far away from the target. If the average speed of the shock wave of this travel path be $v_i$, and another plate $p_j$ 624, with parameters $d_j$ and $v_j$, the time $t_i$ for the shock wave to travel from the i-th plate to the target will be:

$$t_i = d_i/v_i$$

and for the j-th:

$$t_j = d_j/v_j$$

Thus the time difference $t_{ij}$ between the firing of these plates is:

$$t_{ij} = t_i - t_j$$

and the simultaneous arrival of the shock wave fronts at the target can be achieved.

Cradle motion in MRI systems is also electronically controlled and a target organ or area found on localizing images can therefore be positioned in a desired area delimited by the shock wave generator. The supply voltage from the power supply 518 charges the capacitors, found in the driver circuits 520 between firings. A switch element closes the charged capacitor to the plate at the command of the firing control unit 516. The generated acoustic pressure waves must first pass through coupling balloon 514, to reach the surface of the human body 510. At this point the pressure amplitude must be below the pain threshold. On the surface and/or inside of the target 512, the acoustic pressure wave forms a shock wave due to waves arriving in phase. The effect of each and/or a set of shock waves alters the target and for the next firing changes can be implemented based on images made during, interleaved, or after the firings. Specially designed software running on the MRI system computer (and/or on a separate computer) can make these calculations and perform real-time system control as realized by practitioners in the field.

Table 1 has been included to show technical parameters for an experimental model and a clinical system. These values are set forth as exemplary and are not meant to limit the practical scope of the invention.

TABLE 1

| | Technical Parameters | |
|---|---|---|
| | Experimental model | Clinical system |
| Power supply voltage: | 6000 V | (2 - 20) * 6000 V |
| Transducer resistance: | 1 Ohm | (2 - 20) * 0.1 Ohm |

TABLE 1-continued

| | Technical Parameters | |
| --- | --- | --- |
| | Experimental model | Clinical system |
| Transducer inductance: | 1 mH | <0.1 mH |
| Current peak amplitude: | 4000 A | 50000 A |
| MRI field strength: | 0.8 T | 1.5 T |
| Transducer surface area ($A_s$): | | |
| length: | 0.7 m | 20 × 0.05 = 1 m |
| width: | 0.1 m | 2 × 0.05 = 0.1 m |
| Target surface area ($A_t$): | | 0.01 m × 0.01 m |
| $A_s/A_t$: | 700 | 1000 |
| Calculated pressure amplitude | | |
| at the transducer: | 32 kPa | 750 kPa |
| at the target | 22.4 MPa | 750 MPa |
| Measured pressure at the theoretical focal point: | 3.2 +/− 50% MPa | |

While the invention has been described with reference to particular embodiments thereof, those skilled in the art will be able to make various modifications to the described embodiments of the invention without departing from the true spirit and scope thereof. It is intended that MRI systems with electromagnetic transducers and methods which are equivalent to those described herein in that the various elements or steps perform substantially the same function in substantially the same way to accomplish the same result are within the scope of the invention. For example, the transducer design may comprise single-turn wire coils of a flat design. This provides a very low inductance-resistance ratio. A low inductance/resistance ratio means the current in the coils can be turned on very quickly. Fast turn-on means acoustic shock waves can be generated with very short wavelengths. Short wavelengths permit focusing on small objects by optimizing rise time, duration and amplitude of the waves. Such switching may be accomplished by high-voltage, high-amperage solid-state devices.

What is claimed is:

1. An apparatus utilizing the static magnetic field of a magnetic resonance imaging device for generating acoustic pressure waves, comprising:
   a magnetic resource imaging (MRI) device having means for generating a static magnetic field;
   means having a current carrier located in said static magnetic field, for generating a further magnetic field to produce an interaction with said static magnetic field to create a force which acts on said current carrier thereby causing it to move; and
   coupling means located adjacent to said current carrier for converting said motion into acoustic pressure waves.

2. The apparatus of claim 1 wherein:
   said coupling means includes an incompressible fluid.

3. An apparatus according to claim 1, wherein said current carrier comprises a plurality of current carriers arranged in a predetermined spatial relationship adjacent to said coupling means; and
   said means for generating said further magnetic field further comprises:
   supply means for supplying electrical energy to said plurality of current carriers for generating said acoustic pressure waves, wherein said acoustic pressure waves undergo constructive interference at a region thereby creating a focal point;
   storage means for storing said electrical energy; and
   switching means for discharging said electrical energy from said storage means to said plurality of current carriers.

4. An apparatus according to claim 3, further comprising control means for controlling and adjusting timing of said switching means to thereby achieve a temporal firing order, wherein said acoustic pressure waves will produce high pressure at a region determined by at least one of said temporal firing order and said spatial relationship.

5. An apparatus according to claim 4, wherein said MRI device further comprises:
   imaging means for locating a target within a subject;
   means for generating information corresponding to the location of the target; and
   means for communicating said information to said control means, wherein said control means includes means for adjusting said temporal firing order as a function of said information for positioning said focal point to substantially coincide with said target location to thereby cause damage to the target.

6. An apparatus according to claim 5, wherein said MRI imaging means is further adapted to generate NMR images of the subject and interleave said image generation and said generation of said acoustic pressure waves.

7. The apparatus of claim 4 wherein said control means is a computer system.

8. The apparatus of claim 3, further comprising means for spatially positioning said current carriers to cause geometric focusing of said acoustic pressure waves to produce high pressure at a region determined only by said spatial relationship.

9. A method for generating acoustic pressure waves utilizing the static magnetic field of a magnetic resonance imaging device, comprising the steps of:
   generating a static magnetic field using a magnetic resonance imaging device;
   placing a current carrier in said static magnetic field;
   applying a current to said current carrier to generate a further magnetic field to thereby produce an interaction with said static magnetic field, said interaction creating a force which acts on said current carrier thereby causing it to move; and
   placing a coupling means adjacent to said current carrier to thereby generate the acoustic pressure waves.

10. The method of claim 9 further comprising the step of positioning said current carrier within the body of a subject for in vivo generation of said acoustic pressure waves.

11. A method according to claim 9, further comprising the steps of:
   placing a plurality of current carriers in said static magnetic field in a predetermined spatial relationship and located adjacent to said coupling means; and
   applying current to said plurality of current carriers to produce said acoustic pressure waves.

12. A method according to claim 11, further comprising the step of spatially positioning said current carriers to cause geometric focusing of said acoustic pressure waves to produce high pressure at a region determined only by said spatial relationship.

13. A method according to claim 11, further comprising the step of timing the application of said current to said plurality of current carriers to thereby achieve a temporal firing order, wherein said acoustic pressure waves will produce high pressure at a region determined by at least one of said temporal firing order and said spatial relationship.

14. A method according to claim 13, further comprising the steps of:

determining the location of a target within a subject;

generating information corresponding to said target location; and adjusting said temporal firing order for positioning said focal point to substantially coincide with said target location to thereby cause damage to the target.

15. A method according to claim 14, further comprising the step of generating NMR images of the subject.

16. A method according to claim 15, further comprising the step of interleaving said image generation and said generation of said acoustic pressure waves.

* * * * *